United States Patent [19]

Kruithof

[11] Patent Number: 4,918,319
[45] Date of Patent: Apr. 17, 1990

[54] TANNING BED WITH CLOSURE CONTROL MECHANISM

[75] Inventor: Henk P. Kruithof, Grez, Belgium

[73] Assignee: Puretan, Inc., Dallas, Tex.

[21] Appl. No.: 116,452

[22] Filed: Nov. 3, 1987

[51] Int. Cl.4 .............................................. A61N 5/06
[52] U.S. Cl. ............................. 250/504 R; 250/494.1; 250/493.1; 128/395; 128/396; 362/401
[58] Field of Search ............. 250/504 R, 493.1, 494.1; 128/371, 376, 395, 396; 362/402, 401

[56] References Cited

U.S. PATENT DOCUMENTS

| | | | |
|---|---|---|---|
| 4,660,561 | 4/1987 | Nielsen | 250/494.1 |
| 4,683,886 | 8/1987 | Kramer et al. | 128/376 |
| 4,740,707 | 4/1988 | Thaw | 250/494.1 |

FOREIGN PATENT DOCUMENTS

| | | | |
|---|---|---|---|
| 2910865 | 10/1980 | Fed. Rep. of Germany | 128/395 |
| 3533789 | 6/1986 | Fed. Rep. of Germany | 250/504 R |

*Primary Examiner*—Jack I. Berman
*Attorney, Agent, or Firm*—Richards, Medlock & Andrews

[57] ABSTRACT

A tanning bed with a closure control mechanism includes a lower stationery tanning element and an upper moveable tanning element, both mounted between a pair of side arm braces. The side arm braces each have two channels formed therein for slidably receiving a first pair and a second pair of rollers mounted from the upper tanning element. As a result of the orientation of the channels and rollers, the upper tanning element rotates and translates between an opened and a closed position without the need for a counterbalance or motor assist.

26 Claims, 2 Drawing Sheets

TANNING BED WITH CLOSURE CONTROL MECHANISM

TECHNICAL FIELD

This invention relates to a tanning bed and, in particular, to a mechanism for controlling the opening and closing of a tanning bed.

BACKGROUND OF THE INVENTION

Tanning beds have gained in popularity in recent years due, in part, to a societal movement toward better physical conditioning and appearance. Tanning beds are commonly constructed to have a lower, stationary tanning element upon which a person may lie and an upper, movable tanning element. In order for an individual to use such a tanning bed, the upper element must be lifted away from the lower element to permit the individual to place himself on the lower tanning element. It is then necessary to lower the upper tanning element to a position in close relation to the individual for optimal tanning.

Many tanning beds utilize a hinge-type mechanism for attaching the upper tanning element to the lower tanning element. However, due to the overall weight of the upper tanning element, it has been necessary to provide a counterbalancing means to facilitate the raising of the upper tanning element. For example, some tanning beds provide a motor for mechanically raising and lowering the upper tanning element. The use of motors increases the cost of construction as well as the cost of maintaining the tanning bed. In addition, there is a possibility of an individual becoming trapped in the tanning bed as a result of motor failure or a power outage.

Other tanning beds utilize a lifting piston to facilitate the raising of the upper tanning element. The use of a lifting piston also increases the cost of construction. In addition, lifting pistons are prone to fail after a relatively short period of use and therefore must be replaced on a somewhat regular basis, increasing maintenance costs for tanning beds using such devices.

A third method of facilitating the raising of the upper tanning element is to provide a counterbalancing spring or weight which may be connected to the upper tanning element beyond a fulcrum to provide a lever-type counterbalance. Here again there are additional costs in constructing and maintaining such a counterbalancing means.

It is desirable to have a mechanism for raising and lowering the upper tanning element of a tanning bed which utilizes relatively few movable parts, does not require a motor, is simple and inexpensive to construct and maintain, and will not readily wear out under normal use.

SUMMARY OF THE INVENTION

The tanning bed of the present invention comprises a lower, stationary tanning element, an upper, movable tanning element, and a mechanism for controlling the closure of the upper tanning element such that the upper tanning element can be translated and rotated between an opened position and a closed position. The mechanism supporting the upper tanning element comprises two side arm braces, one of which is attached to each end of the lower tanning element. Each brace has first and second channels formed therein adjacent the lower tanning element. A pair of first rollers mounted on the upper tanning element are mounted for movement in the first channels and a pair of second rollers mounted on the upper tanning element are mounted for movement in the second channels.

The first and second channels are oriented such that the upper tanning element may be moved between an opened position, where the upper element is positioned up and away from the lower element, and a closed position, where the upper element is translated downwardly and substantially parallel to the lower element.

BRIEF DESCRIPTION OF THE DRAWINGS

A more complete understanding of the present invention and its advantages will be apparent from the following Detailed Description taken in conjunction with the accompanying drawings, in which.

DETAILED DESCRIPTION

Figure 1:
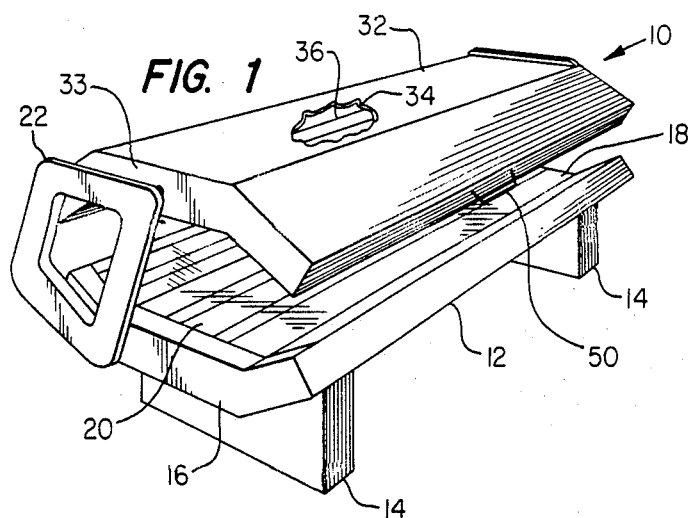
FIG. 1 is a perspective view of the tanning bed of the present invention.

A tanning bed having a closure control mechanism is generally indicated at 10 of FIG. 1. Tanning bed 10 includes stationary lower tanning element 12 fixedly supported by legs 14. Lower tanning element 12 includes lower frame 16, transparent support surface 18, and a plurality of UV lamps 20. Side arm braces 22 are fixedly disposed at each end of lower tanning element 12. Side arm braces 22 may be secured to lower tanning element 12 by any known means such as appropriate bolts or screws. In a preferred embodiment, side arm braces 22 are mounted on lower tanning element 12 using bolts 24.

Figure 3:
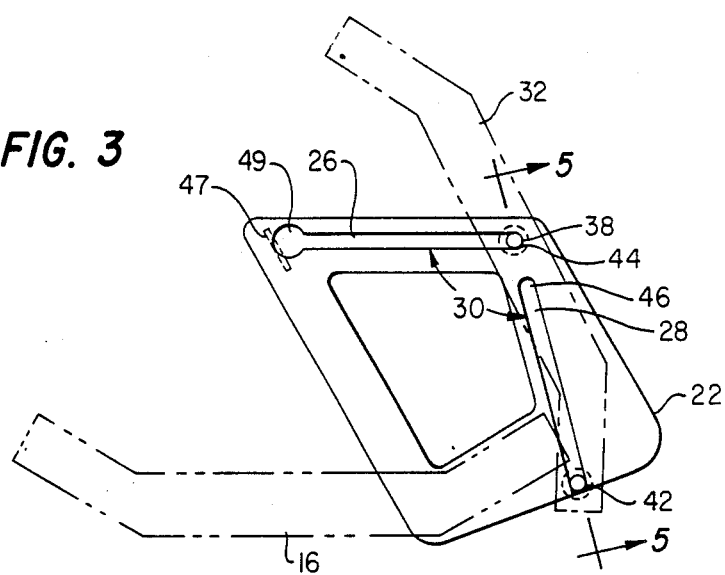
FIG. 3 is a vertical section view of the tanning bed with the tanning elements shown in phantom and showing the upper tanning element in its opened position.

Side arm braces 22 have a first channel 26 and a second channel 28 formed therein on their inner surfaces 25 facing lower tanning element 12. First channels 26 are preferably disposed such that they are substantially horizontal. Second channels 28 are preferably inclined relative to the first channels 26 such that the angle therebetween, depicted at 30 of FIG. 3, is obtuse. It should be appreciated that angle 30 may also measure 90° without changing the nature of the closure control mechanism of the present invention. In the preferred embodiment depicted in FIGS. 3, 4, and 5, angle 30 is obtuse in order to facilitate the opening and closing of tanning bed 10, as discussed in greater detail below.

Figure 2:
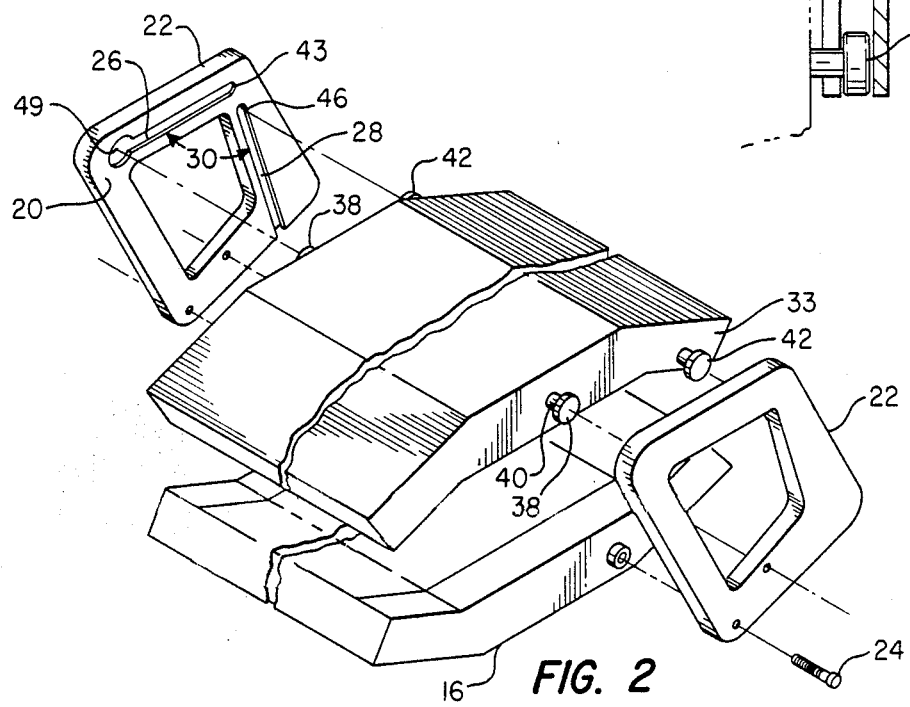
FIG. 2 is a perspective view of the side arm braces exploded away from the upper and lower tanning elements of the tanning bed of the present invention.

Upper tanning element 32 has a configuration substantially identical to that of lower tanning element 12 and includes upper frame 34 and a plurality of UV lamps 36. As best seen in FIG. 2, first rollers 38 are mounted from ends 33 of upper tanning element 32 on shafts 40 using an appropriate bushing. First rollers 38 are preferably mounted on upper tanning element 32 approximately at the center, or centroid, of each end 33. By mounting first rollers 38 in this position, the weight of upper tanning element 32 is evenly balanced on first rollers 38, facilitating rotation of upper tanning element 32. First rollers 38 are retained in first channels 26 such that they roll freely therein. Second rollers 42 are mounted from ends 33 of upper tanning element 32 on shafts 44 using an appropriate bushing. Second rollers 42 are preferably mounted on each end 33 a predetermined distance from first rollers 38. Second rollers 42 are retained in second channels 28 such that they roll freely therein.

In the opened position depicted in FIG. 3, first rollers 38 abut shafts 44 of first channels 26. Also in the opened position, second rollers 42 are positioned, as shown in FIG. 3, near the bottom end of second channels 28. Channels 28 may be dimensioned and second rollers 42 may be positioned on upper tanning element 32 such that second rollers 42 abut terminal ends of second channels 28 when upper tanning element 32 is in the opened position, thus providing support for upper tanning element 32 on first rollers 38 and second rollers 42 rather than only first rollers 38 as shown in FIG. 3. It should be appreciated that in the opened position, upper tanning element 32 is in a condition of inertia and will not tend to move to the closed position of FIG. 4 without the application of force.

Figure 4:
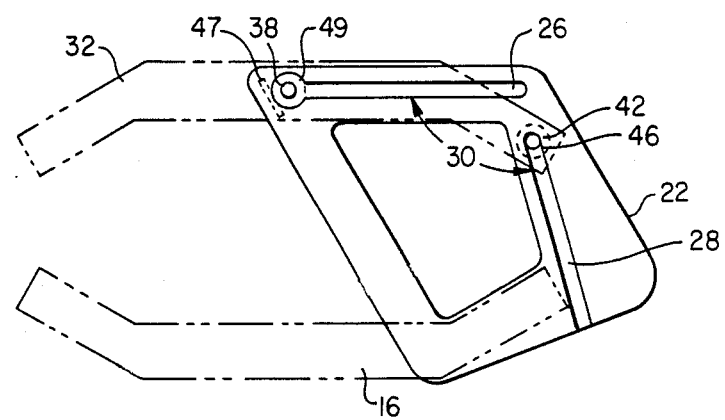
FIG. 4 is a vertical section view of the tanning bed with the tanning elements shown in phantom and showing the upper tanning element in its closed position.

In the closed position depicted in FIG. 4, second rollers 42 abut ends 46 of second channels 28, thus preventing upper tanning element 32 from moving to a hyper-closed position. Also in the closed position, first rollers 38 abut cushion elements 47 disposed in first channels 26 at front ends 49. Cushion elements 47 can be constructed of any suitable material, for example, felt, rubber, etc. It is to be appreciated that first rollers 38 and second rollers 42 are disposed on ends 33 of upper tanning element 32 at a predetermined distance from one another such that first rollers 38 and second rollers 42 simultaneously abut ends of their respective channels 26, 28.

As upper tanning element 32 is moved between its opened and closed positions, it is both rotated and translated as a result of the relative orientations of channels 26, 28 and rollers 38, 42. Because first rollers 38 are positioned midway along edge 33 of upper tanning element 32, the weight of upper tanning element 32 is evenly balanced on first rollers 38. The rotational and translational motion of upper tanning element 32 is further facilitated by constructing side arm braces 22 such that angle 30 is obtuse, thus minimizing the amount of rotation occurring between any two laterally spaced locations on first channel 26. Also, although channels 26 and 28 are shown to be straight along their length, the invention also envisions use of arcuate channels which can facilitate translation of the upper tanning element between its opened and closed positions.

Figure 5:
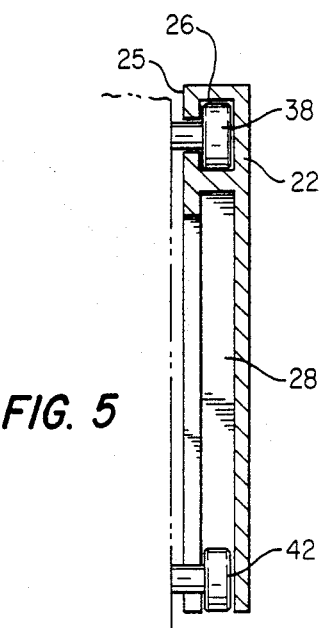
FIG. 5 is a cross-sectional view of the present invention taken along line 5—5 on FIG. 3.

First and second rollers 38, 42 are oriented in channels 26, 28 as shown in FIG. 5. FIG. 5 illustrates a cross-sectional view of a first roller 38 positioned in first channel 26. Channels 26, 28 are C-shaped in order to receive shafts 40, 44 through which rollers 38, 42 are mounted to upper tanning element. Rollers 38, 42 may rotate freely in channels 26, 28 to cause the desired rotational and translational motion of upper tanning element 32.

As can be appreciated by viewing FIGS. 3 and 4, when the upper tanning element is in its opened or raised position, the center of gravity of that portion of the element cantilevered to the side of rollers 38 opposite rollers 42 is substantially through rollers 38. Thus, in the opened position, there is little tendency for the upper element to close without application of force on the element. Moreover, in the opened or raised position, grasping handle 50 on the element provides sufficient leverage to easily translate the element to the closed position.

When the upper element is in the closed position, the center of gravity of that portion of the upper element cantilevered to the side of rollers 38 opposite rollers 42 is more removed from rollers 38 thereby tending to maintain the element in the closed position. However, the sliding and translating movement provided by the rollers and channels in which they move provides for easy opening of the bed. Particularly, the obtuse angle of orientation of channels 28 relative to channels 26 greatly facilitates such movement. It will also be understood that the weight of the upper element and the fit of the rollers in their respective channels, as well as the bushings used with the rollers, are designed such that the upper element will move only upon application of some force thereon and will maintain any position, including intermediate positions between fully opened or closed, in which the element is placed.

The tanning bed closure control mechanism of the present invention can be readily installed on existing tanning beds. Installation of the closure control mechanism on existing beds would require the mounting of side arm braces 22 on lower tanning element 12 and rollers 38, 42 on upper tanning element 32. This procedure would require only a nominal amount of time, effort, and equipment.

Although preferred embodiments of the invention have been described in the foregoing Detailed Description and illustrated in the accompanying drawings, it will be understood that the invention is not limited to the embodiments disclosed, but is capable of numerous rearrangements, modifications, and substitutions of parts and elements without departing from the spirit of the invention. For example, it will be understood by those skilled in the art that the structure as described may be made in a larger or smaller size, in other than a rectangular shape and can be made of materials other than those described. The present invention is therefore intended to encompass such rearrangements, modifications, and substitutions of parts and elements as fall within the scope of the invention.

What is claimed is:

1. In a tanning bed having an upper tanning element having a pair of oppositely facing end surfaces and a lower tanning element, a closure control mechanism comprising:
   a pair of side arm braces, one said brace mounted at each end of said lower tanning element;
   a first channel and a second channel defined on each said brace;
   a pair of first rollers mounted on said upper tanning element and positioned for movement in said first channels; and
   a pair of second rollers mounted on said upper tanning element and positioned for movement in said second channels, whereby said upper tanning element can be rotated and translated relative to said lower tanning element between a first, opened position and a second, closed position.

2. The tanning bed of claim 1 wherein said first channels are substantially horizontal and said second channels are inclined relative to said first channels.

3. The tanning bed of claim 1 wherein said first channels and said second channels have an opening facing inwardly toward the tanning elements.

4. The tanning bed of claim 1 wherein said first rollers are mounted on first shafts, and wherein said second rollers are mounted on second shafts, said first shafts and said second shafts being mounted on said upper tanning element.

5. The tanning bed of claim 1 wherein said first pair of rollers are mounted on said upper tanning element at the centroids of said end surfaces of said upper tanning element.

6. The tanning bed of claim 1 wherein said first pair and said second pair of rollers are disposed on said upper tanning element at a predetermined distance from one another, whereby said first pair of rollers engages terminal ends of said first channels in said opened position and said first pair and said second pair of rollers engage terminal ends of said first channels and said second channels in said closed position.

7. A tanning bed comprising:
 a lower tanning element having a transparent body-supporting surface and a plurality of ultraviolet lamps disposed therein beneath said body-supporting surface;
 an upper tanning element having a pair of oppositely facing end surfaces and a plurality of ultraviolet lamps disposed therein; and
 a closure control mechanism, said closure control mechanism comprising a pair of side arm braces, one said side arm brace disposed at each end of said lower tanning element, channel means defined in each side arm brace for receiving slide means mounted on each end of said upper tanning element, said slide means positioned for movement in said channel means between an opened and closed position.

8. The tanning bed of claim 7 wherein said channel means includes a horizontal portion.

9. The tanning bed of claim 7 wherein said channel means includes an inclined portion.

10. The tanning bed of claim 7 wherein said channel means open inwardly toward said tanning elements.

11. The tanning bed of claim 7 wherein said slide means are mounted at the centroids of said end surfaces of said upper tanning element.

12. The tanning bed of claim 7 wherein a second pair of slide means are mounted on said end surfaces of said supper tanning element and positioned for movement in said channel means.

13. The tanning element of claim 12 wherein one pair of said slide means is mounted at the centroids of said end surfaces of said upper tanning element.

14. In a tanning bed having an upper tanning element with a pair of oppositely facing end surfaces and a lower tanning element, a closure control mechanism comprising:
 a pair of side arm braces, one said brace mounted at each end of said lower tanning element;
 channel means defined on each said brace adjacent the ends of said tanning elements; and
 slide means mounted on the end surfaces of upper tanning element and positioned for movement in said channel means between an opened and closed position.

15. The tanning bed of claim 14 wherein said channel means includes a horizontal portion.

16. The tanning bed of claim 14 wherein said channel means includes an inclined portion.

17. The tanning bed of claim 14 wherein said channel means open inwardly toward said tanning elements.

18. The tanning bed of claim 14 wherein said slide means are mounted at the centroids of said end surfaces of said upper tanning element.

19. The tanning bed of claim 14 wherein a second pair of slide means is mounted on said end surfaces of said upper tanning element and positioned for movement in said channel means.

20. The tanning bed of claim 14 wherein one pair of said slide means is mounted at the centroids of said end surfaces of said upper tanning element.

21. In a tanning bed having an upper tanning element having a pair of oppositely facing end surfaces and a lower tanning element, a closure control mechanism comprising:
 a pair of arm braces, one said brace mounted at each end of said lower tanning element;
 a first channel and a second channel defined on each said brace;
 a pair of first slide means mounted on said end surfaces of said upper tanning element and positioned for movement in said first channels; and
 a pair of second slide means mounted on said ends of said upper tanning element and positioned for movement in said second channels.

22. The tanning bed of claim 21 wherein said first channels and said second channels face inwardly toward said tanning elements.

23. The tanning bed of claim 21 wherein said second channels are inclined relative to said first channels.

24. The tanning bed of claim 21 wherein said first channels are perpendicular to said second channels.

25. The tanning bed of claim 21 wherein said first slide means are mounted on said upper tanning element at the centroids of said end surfaces of said upper tanning element.

26. The tanning bed of claim 21 wherein said first slide means and said second slide means are disposed on said upper tanning element at a predetermined distance from one another, whereby said first slide means engages terminal ends of said first channels in an opened position and said first slide means and said second slide means engage terminal ends of said first channels and said second channels in a closed position.

* * * * *